United States Patent [19]

Towse

[11] 4,392,499
[45] Jul. 12, 1983

[54] ADAPTOR FOR FACILITATING BLOOD SAMPLING PROCEDURES

[76] Inventor: Eric R. Towse, 647 74 St., Brooklyn, N.Y. 11209

[21] Appl. No.: 269,261

[22] Filed: Jun. 1, 1981

Related U.S. Application Data

[63] Continuation of Ser. No. 50,601, Jun. 21, 1979, abandoned.

[51] Int. Cl.³ ............................................. A61B 5/14
[52] U.S. Cl. .................................... 128/764; 604/283; 604/243
[58] Field of Search ..................... 128/214.4; 604/243, 604/283

[56] References Cited

U.S. PATENT DOCUMENTS

| | | | |
|---|---|---|---|
| 2,531,667 | 11/1950 | Brent | 128/214.4 |
| 2,689,564 | 9/1954 | Adams et al. | 128/214 R |
| 3,181,529 | 5/1965 | Wilburn | 128/764 |
| 3,433,215 | 3/1969 | Silverman | 128/768 |
| 3,616,789 | 11/1971 | Grabhorn | 128/764 X |
| 3,739,778 | 6/1973 | Monestere, Jr. et al. | 128/214.4 |
| 3,753,432 | 8/1973 | Guerra | 128/764 |
| 4,140,108 | 2/1979 | Nugent | 128/760 |
| 4,192,919 | 3/1980 | Raghanacharia | 128/764 X |

Primary Examiner—George F. Lesmes
Assistant Examiner—Nancy A. B. Swisher
Attorney, Agent, or Firm—Schwartz & Weinrieb

[57] ABSTRACT

A tubular adaptor is adapted to be interposed between an intravenous catheter and a needle carried by a tube holder for housing an evacuated tube for blood-sampling purposes. The adaptor is readily separable from the catheter by means of a tapered-socket fitting, and in this manner, either blood-sampling or intravenous-feeding may be accomplished at the same catheterized situs. The needle and evacuated tube assemblage are isolated from the situs by means of the adaptor and catheter. The flexibility of the catheter tube also serves to isolate the assemblage from the situs whereby adverse effects created by the assemblage during sampling procedures are not impressed upon the situs.

6 Claims, 1 Drawing Figure

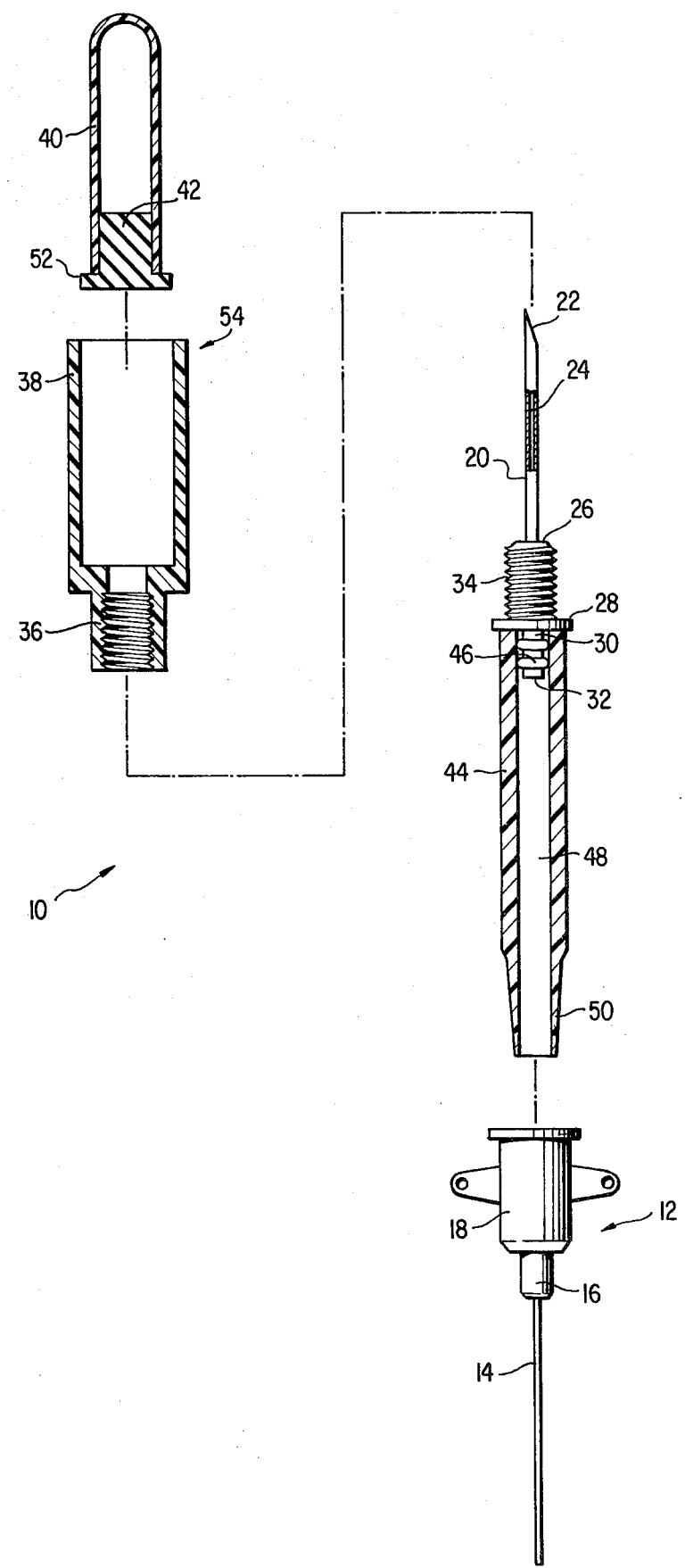

ADAPTOR FOR FACILITATING BLOOD SAMPLING PROCEDURES

This is a continuation of application Ser. No. 50,601, filed on June 21, 1979, now abandoned.

FIELD OF THE INVENTION

The present invention relates generally to blood collecting apparatus, and more particularly, to blood collecting apparatus which includes an adaptor capable of operatively mating with an intravenous catheter such that blood sampling operations may be directly achieved from the catheterized site.

BACKGROUND OF THE INVENTION

The withdrawal and analysis of blood is a common procedure often performed, for example, within hospital facilities as a prelude to the administration of intravenous solutions. A conventional means utilized to accomplish such procedure comprises an evacuated tube constructed, for example, of glass and having a sterilized interior for receiving the blood sample. The open end of the tube is sealed by means of a rubber stopper, and the sealed tube is adapted to be disposed within a tube holder in order to accomplish the blood sampling procedure. A double-ended needle, having an axial bore defined therein, is threadedly secured to the tube holder, and in a conventional manner, the proximal end of the needle is employed to penetrate the individual's vein while the distal end of the needle will subsequently penetrate the evacuated tube stopper. As a result of the pressure differential defined between the evacuated tube and the blood vessel, blood flows from the individual's vein, through the needle, and into the sampling tube.

It is often necessary to take multiple blood samples from the individual in order to perform a battery of laboratory tests. As a matter of procedure, the double-ended needle is maintained within the person's vein while the evacuated tubes are simply interchanged in a successive manner by removing the filled tubes from the tube holder and replacing the same with empty tubes. As the insertion and removal of the distal end of the needle into and out of the sealing stopper is not always readily accomplished in a simple and easy manner, the individual may be subjected to a substantial amount of discomfort. In addition, tissue damage within the vein-puncture situs is also a likely deleterious side effect of the foregoing blood sampling procedure.

Subsequent to the blood sampling procedure, intravenous feeding of solutions or medications is often established as the requirements of the particular patient dictate. A catheter is conventionally employed for accomplishing intravenous feeding operations, and as this procedure is entirely separate from the blood sampling procedure, the catheter is normally inserted into a region of the patient wholly dissociated from the blood-sampling situs, or within the region of the sampling situs, as convenience may warrant. Nevertheless, the insertion of the catheter is accomplished by means of a needle cannula-catheter assembly which is separate and distinct from the blood-sampling needle. As a result, it is readily appreciated that at least two vein-puncture sites must be established in order to accomplish both the blood-sampling and intravenous-feeding procedures. Such techniques, of course, subject the individual to multiple periods of discomfort, and increase the likelihood of tissue damage.

OBJECTS OF THE INVENTION

Accordingly, it is an object of the present invention to provide new and improved blood collecting or sampling apparatus.

Another object of the present invention is to provide new and improved blood sampling apparatus which will overcome the various disadvantages of prior art apparatus.

Still another object of the present invention is to provide new and improved blood sampling apparatus which will permit multiple blood-sampling procedures to be achieved with a greater degree of comfort imparted to the patient.

Yet another object of the present invention is to provide new and improved blood sampling apparatus which will substantially reduce the amount of tissue damage to which the patient may be subjected during blood-sampling and intravenous-feeding procedures.

Still yet another object of the present invention is to provide new and improved apparatus which will permit both blood-sampling and intravenous-feeding procedures to be accomplished by means located at or within the same vein-puncture situs.

SUMMARY OF THE INVENTION

The foregoing and other objectives are achieved in accordance with the present invention through the provision of a tubular adaptor the proximal end of which is adapted to be mated with a plastic intravenous catheter disposed within the patient's vein, while the distal end of the adaptor has a needle disposed therein and projecting axially outwardly therefrom. The needle is adapted to be threadedly secured within an evacuated tube-holder conventionally employed to house an evacuated tube during blood-sampling procedures.

The adaptor is readily separable from the catheter, and as a result, the blood-sampling, as well as subsequent intravenous-feeding procedures may be accomplished at the same catheterized situs. The flexibility of the catheter tube substantially reduces the discomfort experienced by the patient during the blood-sampling procedures due to the fact that any difficulty encountered in inserting or removing the distal end of the needle into and out of the stopper of the evacuated tube does not adversely affect the intravenous situs. The forces affecting the needle assembly are isolated from the intravenous situs as a result of the assembled relationship defined between the adaptor and the catheter, as well as the flexibility of the catheter tube. Consequently, the problems characteristic of the prior art apparatus wherein the proximal end of the rigid needle is inserted directly within the intravenous puncture situs are overcome.

BRIEF DESCRIPTION OF THE DRAWINGS

Various other objects, features, and attendant advantages of the present invention will be more fully appreciated as the same becomes better understood from the following detailed description when considered in connection with the accompanying drawings, wherein:

The SOLE FIGURE is an exploded view, partly in cross-section, of the blood-sampling apparatus of the present invention and showing its cooperative parts.

DETAILED DESCRIPTION OF THE PREFERRED EMBODIMENT

Referring now to the drawing, there is shown, in combination, the blood-sampling apparatus of the present invention, the same being generally indicated by the reference character 10. The apparatus includes a plastic catheter, generally indicated by the reference character 12, which comprises a flexible tube 14 the distal end of which is fixedly secured within a hub portion 16. The hub 16 is integrally formed with a female socket 18 the interior configuration of which tapers radially inwardly as one proceeds from the distal end of the socket toward the proximal end thereof, or alternatively, as one proceeds from right to left as viewed in the FIGURE.

A needle 20, having a sharpened distal end 22 and an axial bore 24 defined therethrough, is fixedly secured within a hub 26. Hub 26 terminates at a flanged portion 28, and a boss 30 projects axially away from flanged portion 28 in a direction opposite that in which hub 26 extends. Boss 30 is coaxially aligned with hub 26, and the non-pointed, proximal end 32 of needle 20 projects axially outwardly of boss 30.

The external surface of hub 26 is provided with threads 34 which are adapted to threadedly engage an internally threaded neck portion 36 of a conventional evacuated tube-holder 38. The tube-holder 38 is, of course, adapted to separably house a removable conventional evacuated tube 40 having a rubber sealing stopper 42 fixedly secured within the open end thereof.

In lieu of needle 20, conventional prior art apparatus employs a needle the opposite ends of which are both pointed or sharpened, the distal end corresponding to end 22 of needle 20, while the proximal end thereof is adapted to penetrate the patient's vein in order to facilitate the intravenous withdrawal of blood for the sampling purposes. Such apparatus exhibits disadvantageous characteristics, however, as more fully noted hereinabove, due particularly to the fact that the proximal end of the rigid needle is directly inserted within the patient's vein.

In accordance with the present invention, the proximal, non-pointed end 32 of the needle is disposed within boss 30 of the needle hub assembly, and it is seen that the boss 30 is disposed within the distal end of a plastic, tubular adaptor 44. The external surface of boss 30 is provided with peripherally extending ribs 46 for frictionally engaging the interior wall surfaces of adaptor 44 whereby the needle assembly will be firmly retained within the adaptor. The bore 48 of adaptor 44 is, of course, in fluidic communication with the proximal end 32 of needle 20, and the proximal end 50 of adaptor 44 is adapted to be in fluidic communication with the catheter socket 18. In order to facilitate the mating engagement of adaptor 44 with catheter socket 18, the external surface of the proximal end 50 of adaptor 44 has a reduced diameter and is tapered radially inwardly in a manner corresponding to that of the interior of socket 18 as noted hereinbefore.

In utilizing the apparatus of the present invention, the catheter 12 is initially inserted into the patient at a selected intravenous situs by means of a conventional needle cannula-catheter assembly, and subsequent to the withdrawal of the needle cannula, the catheter 12 is readily available for the commencement of blood-sampling or intravenous-feeding procedures. If both blood-sampling and intravenous-feeding procedures are in fact to be conducted, the blood-sampling operations should be conducted prior to the intravenous-feeding operations.

Consequently, with the catheter 12 already positioned within the patient at the particular situs, the adaptor 44, along with the needle 20, is mated with the catheter. Subsequently, when a blood sample is to be taken, the tube-holder 38 is threadedly mated to the hub 26. It is to be noted that the length of needle 20, relative to the length of the sleeve-type housing comprising tube-holder 38, is such that upon full threaded engagement between hub 26 and holder neck portion 36, the distal end 22 of needle 20 will still be axially disposed within holder 38 and will not protrude axially therebeyond.

When the catheter-adaptor-needle-tube holder assemblage is established, the evacuated tube 40 may then be inserted within the tube holder 38. The diametrical extent of the annular flanged portion 52 of stopper 42 is such that a sealing fit is established between portion 52 and the interior wall surfaces of holder 38. Continued movement of the tube in the direction of arrow 54 will force the distal end 22 of needle 20 to penetrate the stopper 42 whereby a pressure differential is established between the evacuated atmosphere of tube 40 and the pressurized environment of the patient's vein. Blood will thus flow from the vein, through catheter 12, through the adaptor 44, through needle 20, and into tube 40.

When tube 40 becomes filled, the stopper 42 may be disengaged from needle 20 and the tube 40 removed from holder 38. If required, additional tubes 40 may be filled by repeating the aforenoted operational procedures, or alternatively, when the last 40 has been filled, the entire adaptor assemblage may be disconnected from catheter 12, and subsequently, a particular intravenous solution may be operatively connected to the catheter.

As can readily be appreciated, the interexchange of the tubes 40 in fulfillment of the multiple blood-sampling requirements can be accomplished by means of the adaptor apparatus of the present invention without any substantial discomfort being imparted to the patient due to the fact that the flexible catheter tube 14 is disposed within the patient at the intravenous situs as opposed to a rigid needle cannula. Consequently, the forces impressed upon the entire assemblage during replacement of a filled tube 40 with a new evacuated tube 40 are isolated from the intravenous situs thereby eliminating any substantial degree of discomfort to the patient.

Similarly, when the blood-sampling procedures are completed and it is desired to establish intravenous feeding, the blood-sampling assemblage is simply disconnected from the catheter and the intravenous feed tube, not shown, is operatively connected to catheter 12 in a manner similar to the connection procedure utilized in connecting the adaptor 44 to catheter 12. In this manner, the same catheterized situs is employed for both the blood-sampling and intravenous-feeding procedures, and the patient is relieved of the further discomfort of establishing an intravenous situs separate and distinct from the blood-sampling situs as is characteristic of prior art techniques.

Obviously, many modifications and variations of the present invention are possible in light of the foregoing teachings. It is therefore to be understood that within the scope of the appended claims, the present invention may be practiced otherwise than as specifically described herein.

What is new and desired to be secured by Letters Patent of the United States is:

1. Apparatus for facilitating both intravenous and blood-sampling procedures, comprising:
    evacuated tube means for collecting a blood sample;
    needle means operatively connected with said tube means for supplying said blood sample thereto;
    an adaptor releasably connected with said needle means for transferring said blood sample from a catheter to said needle means; and
    a flexible intravenous catheter having a socket means integrally bound therewith, said socket means constructed to separably receive said adaptor to form a temporary connection with said catheter so as to be able to withdraw blood from a mammalian blood vessel and said socket means being readily connectable to a source of intravenous fluid when said adaptor is not connected to said catheter;
    whereby said catheter may be utilized to perform both said blood-sampling and intravenous-feeding procedures without removing said catheter from a blood vessel such that intravenous feeding takes place at the blood-sampling site.

2. The apparatus as set forth in claim 1, wherein:
    said socket means is tapered at the distal end thereof the proximal end of said adaptor is tapered in a manner corresponding to that of said tapered socket.

3. The apparatus as set forth in claim 1, wherein:
    said adaptor is a tube interposed between said catheter means and said needle means.

4. The apparatus as set forth in claim 1, wherein:
    said socket means has a tapered configuration; and
    the proximal end of said adaptor is tapered in a manner corresponding to that of said tapered socket means.

5. The apparatus as set forth in claim 1, further comprising a tube holder for holding said evacuated tube during said blood-sampling procedure.

6. The apparatus as set forth in claim 5, wherein:
    said adaptor is a tube interposed between said catheter and said needle means.

* * * * *